United States Patent
Qian

(10) Patent No.: US 9,669,082 B2
(45) Date of Patent: *Jun. 6, 2017

(54) PROTEINASE-ENGINEERED CANCER VACCINE INDUCES IMMUNE RESPONSES TO PREVENT CANCER AND TO SYSTEMICALLY KILL CANCER CELLS

(71) Applicant: Yong Qian, San Diego, CA (US)

(72) Inventor: Yong Qian, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/594,166

(22) Filed: Jan. 11, 2015

(65) Prior Publication Data

US 2015/0132285 A1    May 14, 2015

Related U.S. Application Data

(63) Continuation-in-part of application No. 12/322,237, filed on Jan. 31, 2009, now abandoned, which is a continuation-in-part of application No. 11/638,747, filed on Dec. 14, 2006, now abandoned, said application No. 13/322,237 is a continuation-in-part of application No. 11/825,246, filed on Jul. 5, 2007, now abandoned, which is a continuation-in-part of application No. 11/542,442, filed on Oct. 3, 2006, now abandoned.

(60) Provisional application No. 60/752,140, filed on Dec. 19, 2005, provisional application No. 60/723,499, filed on Oct. 3, 2005.

(51) Int. Cl.
*A61K 39/00* (2006.01)

(52) U.S. Cl.
CPC .. *A61K 39/0011* (2013.01); *A61K 2039/5152* (2013.01)

(58) Field of Classification Search
None
See application file for complete search history.

(56) References Cited

U.S. PATENT DOCUMENTS

| | | | |
|---|---|---|---|
| 4,844,897 A * | 7/1989 | Maeda | C12N 9/96 424/94.3 |
| 7,247,310 B1 * | 7/2007 | Ohno | A61K 39/0011 424/277.1 |
| 2002/0081596 A1 * | 6/2002 | Lillie | C12Q 1/6886 435/6.16 |

FOREIGN PATENT DOCUMENTS

WO   WO 9634941 A1 * 11/1996 ......... A61K 38/4873

OTHER PUBLICATIONS

Houck et al., Biochem. Biophys. Res. Commun., 1987, 145(3):1205-1210.*

* cited by examiner

*Primary Examiner* — Hong Sang
(74) *Attorney, Agent, or Firm* — Lili Chen

(57) ABSTRACT

The present invention provides a method of making a proteinase-engineered cancer vaccine for treating a cancer patient, especially for cancer patient at advanced/metastatic stage. The cancer vaccine comprises dead cancer cells with unbroken plasma membrane wherein the extracellular proteins and extracellular portion of membrane proteins are cleaved by proteinase digestion. The cancer vaccine may be derived from cancer cell lines or patients' cancer cells. The present invention provides a method of treating a cancer patient by administrating an effective amount of the cancer vaccine to the patient. In a clinical trial with 35 cancer patients, the cancer vaccine therapy brings cancer-free lives (no detectable tumor, micro tumor or cancer cells after treatments of customized cancer vaccines) back to 40% of these patients. The present invention further provides a method of obtaining cancer-specific immune components from blood of individuals treated with the cancer vaccine.

5 Claims, 6 Drawing Sheets

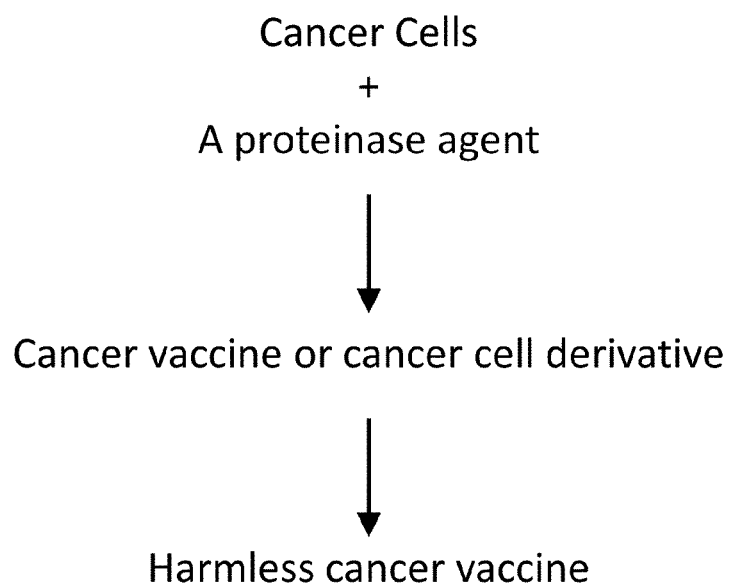
FIG. 1 Schematic illustration of using a proteinase agent to create a harmless cancer vaccine capable of inducing immune responses against cancer cells

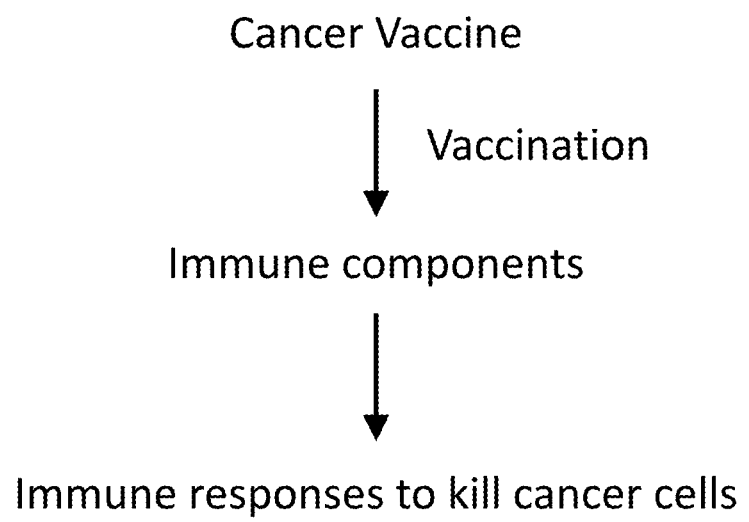
FIG. 2 Schematic illustration of using a harmless cancer vaccine to vaccinate individuals to produce immune components and immune responses to kill cancer cells

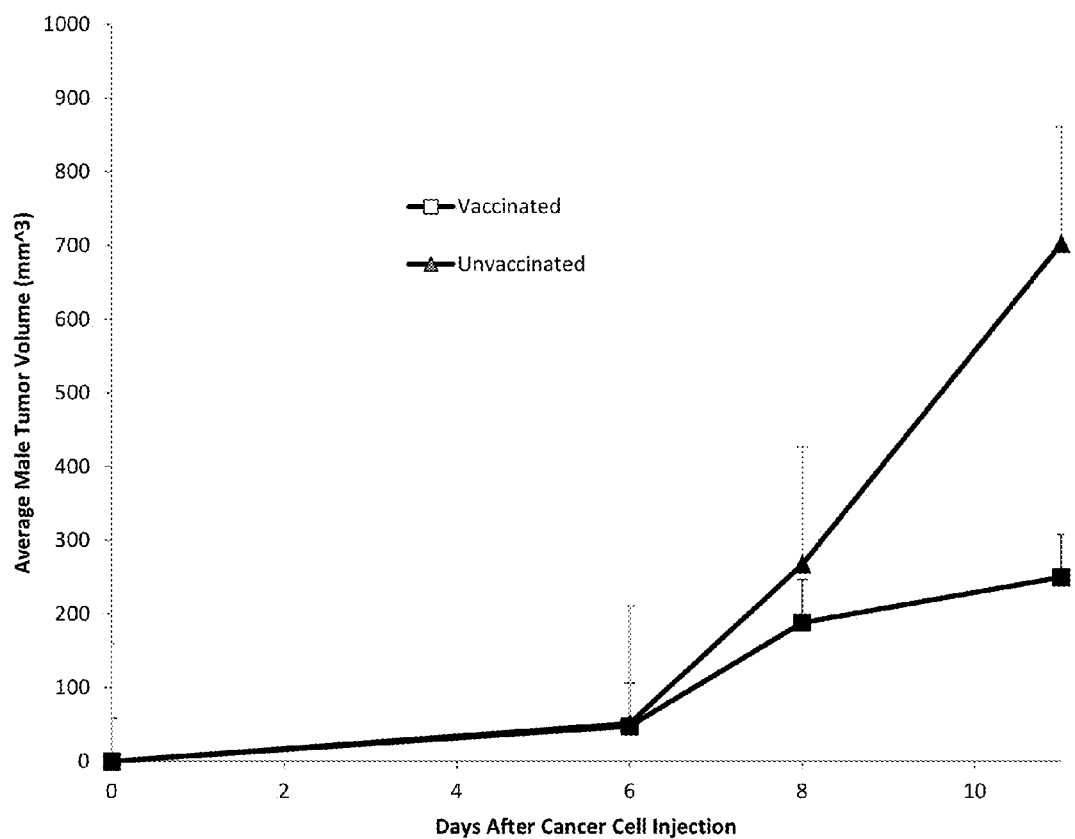
FIG. 3 Tumor growth chart showing cancer vaccine vaccinated male mice induced immune responses against tumor cancer cells vs. unvaccinated male mice which did not induce immune responses against cancer cells' malignant tumor growth

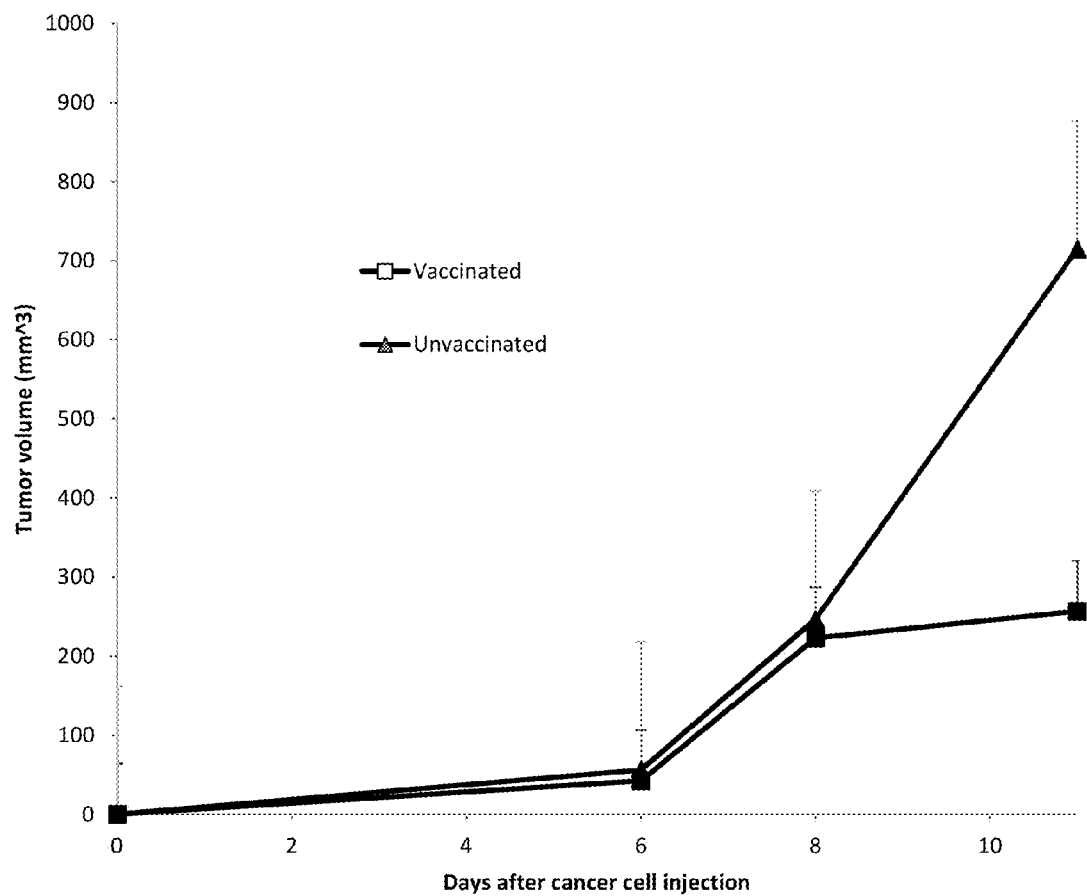
FIG. 4 Tumor growth chart showing cancer vaccine vaccinated female mice induced immune responses against cancer cells' tumor growth vs. unvaccinated female mice which did not induce immune responses against cancer cells' malignant tumor growth

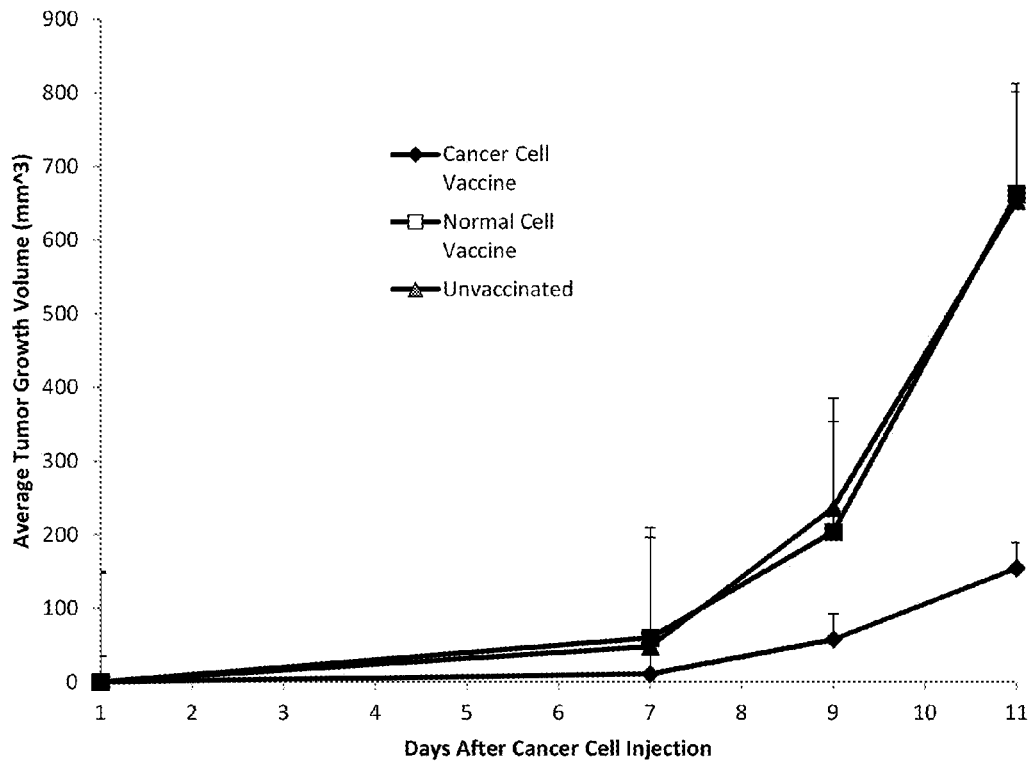
FIG. 5 Tumor growth chart showing cancer vaccine vaccinated mice induced immune responses against cancer cells' tumor growth vs. normal cell "vaccine" vaccinated mice and unvaccinated mice which did not induce immune responses against cancer cells' malignant tumor growth

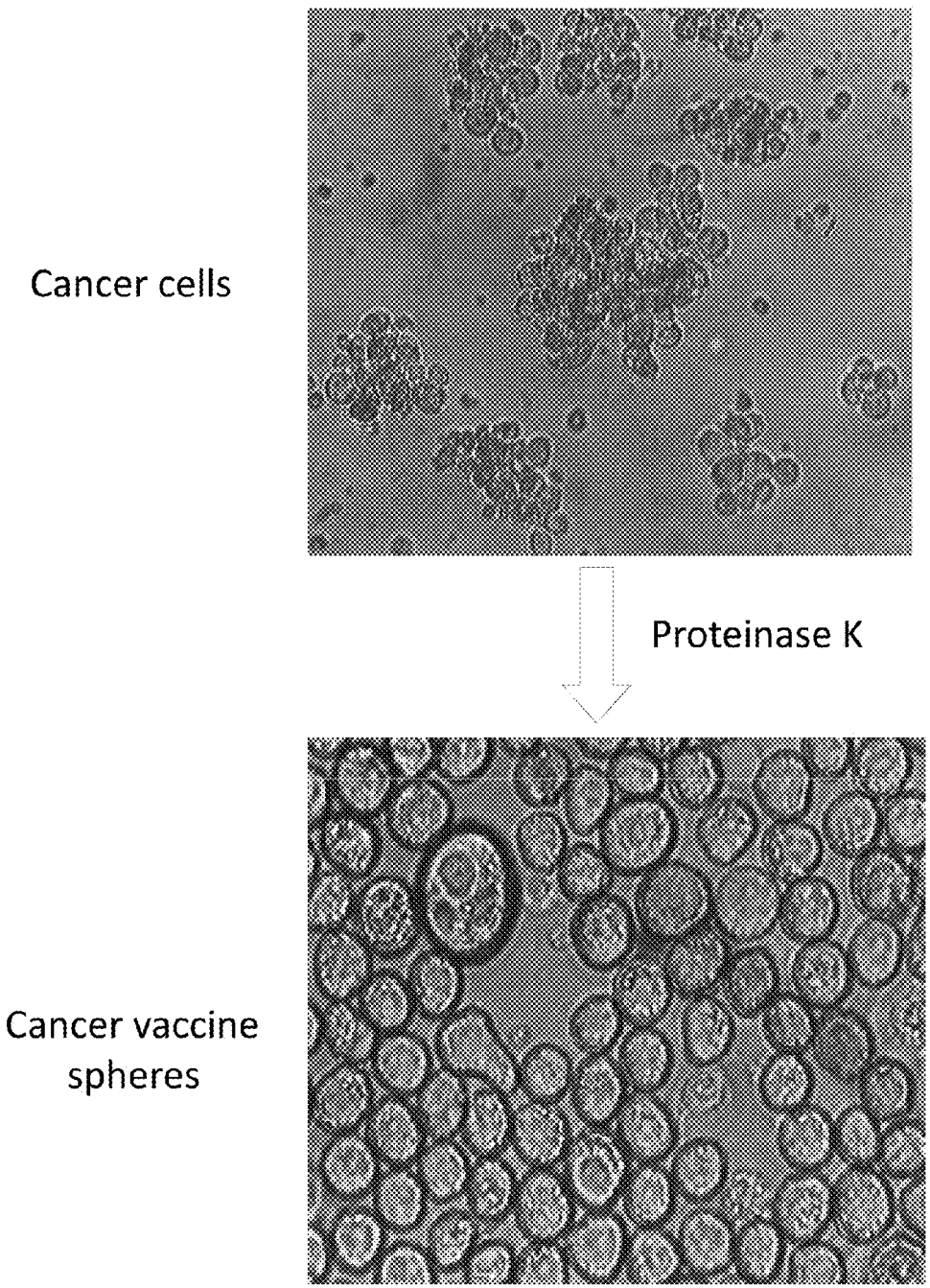
FIG 6, Proteinase K-treated cancer vaccine spheres form round-shaped "giant liposome", which contains all the intracellular cancer-specific antigens

US 9,669,082 B2

PROTEINASE-ENGINEERED CANCER VACCINE INDUCES IMMUNE RESPONSES TO PREVENT CANCER AND TO SYSTEMICALLY KILL CANCER CELLS

CROSS-REFERENCE TO RELATED APPLICATIONS

This patent application is a continuation-in-part of U.S. patent application Ser. No. 12/322,237, filed Jan. 31, 2009, now abandoned, which is a continuation-in-part of U.S. application Ser. No. 11/638,747, filed Dec. 14, 2006, now abandoned, which claims the benefit of priority to U.S. provisional application No. 60/752,140, filed Dec. 19, 2005. Each of the above applications is incorporated by reference herein in its entirety.

This patent application is a continuation-in-part of U.S. patent application Ser. No. 12/322,237, filed Jan. 31, 2009, now abandoned, which is a continuation-in-part of U.S. application Ser. No. 11/825,246, filed Jul. 5, 2007, now abandoned, which is a continuation-in-part of U.S. application Ser. No. 11/542,442, filed Oct. 3, 2006, now abandoned, which claims the benefit of priority to U.S. provisional application No. 60/723,499, filed Oct. 3, 2005. Each of the above applications is incorporated by reference herein in its entirety.

STATEMENT REGARDING FEDERALLY SPONSORED RESEARCH OR DEVELOPMENT

This invention was not sponsored by any federal research or development fund.

BACKGROUND OF THE INVENTION

The idea of using proteinases to do solid-tumor microsurgery has led to the discovery of a new class of drugs that can eliminate solid-tumors by destroying the solid-structure of the main tissue of the tumor and kill actively-dividing cells locally[2]. Basically, proteinases are employed to digest extracellular proteins including the extracellular domains of cell membrane proteins within a tumor. This kills actively dividing cells including cancer cells locally so as to eliminate a tumor as an organ. Desired outcomes are to eliminate tumor organs before cancer metastasis. However, due to some known reasons (such as irregular tumor shapes, locations, types and stages of the cancer, metastasis, proteinase species used and the surrounding tissue or organ microenvironment around the tumor) and other unknown reasons, the proteinase biochemotherapy may not be able to kill all cancer cells, especially in cases of metastasis. The untreated cancer cells may continue to grow and to metastasize to form new tumor organs. If the immune system is programmed with information against cancer cells by previous vaccination with a cancer vaccine, the proteinase biochemotherapy would be more effective because the immune system will kill any untreated or metastasized cancer cells for potential cure.

Cancer causes, types, races, diagnoses, treatments and challenges have been previously described[1, 2]. However, challenges in developing an immunotherapy to treat cancer patients can be further addressed. First of all, a solid-tumor is an organ composed of a main tissue of cancer cells packed and networked together by over-expressed extracellular proteins which form a solid structure, and sporadic tissues of actively-dividing normal cells and blood vessels. Sporadic tissues were recruited by the main tissue to support the growth of the tumor organ. Secondly, the solid-structure of the main tissue of the tumor organ traps macrophages to disrupt their antigen-presentation processes. Thirdly, the tumor organ expresses and over-expresses cytokines and interleukins that drive immune screening cells including dendritic cells, B-cells, T-cells, natural killer cells and monocytes away from the organ. These events further disrupt the immune system's antigen sampling and presentation processes. Fourthly, the expression and over-expression of self-recognition molecular patterns by cancer cells prevents the immune system from obtaining cancer cells' mutation information. Thus, chemotherapy small molecules, immunotherapy monoclonal antibodies and T-cells are not effective enough against cancer if the tumor organ is not disrupted or eliminated. Proteinase-based biochemotherapy can quickly (within hours) and effectively eliminate the malignant solid-tumor organ locally[2]. However, the immune system takes weeks to work pro-actively against cancer cells. There is an urgent need to pre-program the immune system to fight against cancer cells more quickly. Furthermore, the difference between extracellular matrices of cancer cells and that of actively dividing normal cells is not significant enough for the immune system to recognize. There is a great need to alter the self-recognition molecular patterns on the surfaces of cancer cells and expose their cancer cell specific mutation information for the body's immune system (via various lymphocytes) to recognize, sample, present, compare, process and eventually memorize in order to make cancer vaccine induced immune responses working against cancer cells.

BRIEF SUMMARY OF THE INVENTION

A proteinase-engineered harmless cancer vaccine is invented for prevention and potential cure of cancer. A proteinase is used to make a cancer vaccine by altering cancer cells' self-recognition molecular patterns on cancer cell surfaces leaving the cell membrane intact. The vaccine is harmless to normal healthy cells and will not transform normal cells to cancer cells. The cancer vaccine induces immune responses against cancer cells using shared mutation information in the vaccine and cancer cells. The cancer vaccine may be used for cancer prevention for both healthy and pre-cancer high-risk individuals. It can be used as an immunotherapy drug for a cancer patient if the genetic or antigen mutation information in the cancer vaccine is the same or similar to that in the patient's cancer cells. The vaccine may also be useful for cancer patients who may undergo biochemotherapy using the same or different proteinase agent(s) for solid-tumor elimination locally because proteinases can disrupt or destroy the solid-structure of a malignant solid tumor and the cancer vaccine induced immune responses can kill any remaining cancer cells for a potential cure. Furthermore, some proteinases can kill cancer cells directly and others cannot[2], those that are not able to kill cancer cells by themselves may be used to destroy the solid-structure of malignant solid tumor organs in immunized cancer patients allowing the immune system to kill remaining cancer cells for a potential cure. The proteinase agent may be any proteinase that can alter the conservative self-recognition molecular patterns of cancer cells but maintain mutation information in their cancer associated antigens which may include but is not limited to over-expression of one to multiple onco-genes, loss of tumor suppressor genes, tumor promoting microRNAs, heterogeneous, unstable or mutating genomes and associated gene over-expression patterns.

Cancer vaccines may be made from cancer cells that derived from cultured cancer cell lines or from cancer patients directly. When these vaccines are used to immunize healthy or high-risk individuals, cancer cell mutation information is entered into their immune systems. These systems will be able to kill cancer cells according to their acquired mutation information. Thus, cancer within the mutation range of the cancer vaccine will be prevented. The cancer vaccine specific immune components including polyclonal antibodies made against cancer vaccines, and lymphocytes including B-cells, natural killer cells, T-cells and macrophages involved in the immune responses against target cancer cells, may be obtained from the blood of immunized individuals. Concentrated or purified cancer vaccine specific immune components may be used as therapeutic agents to help a cancer patient's immune system to fight against cancer cells. Individual animal or human cancer patients may be injected with the cancer vaccine via subcutaneous (sub-Q) once a week for five consecutive weeks or more until all cancer cells are killed. When needed, multiple cancer vaccines may be used to vaccinate cancer patients and healthy individuals as well. A local biochemotherapy tumor elimination drug such as Tumorase™ (U.S. Pat. No. 3,795,961, Biomedicure, San Diego, Calif.) which has proteinase K as the active ingredient or other proteinase agents may be used in combination with the cancer vaccine to eliminate malignant solid tumor organs. When most, if not all, malignant solid-tumor cancer cells are digested extracellularly by a proteinase, cancer cells will be killed either by the proteinase agent or the activated immune responses. These and other objects, advantages, and features of the invention will be better understood by reference to the several views of drawings and the detailed descriptions of the invention.

BRIEF DESCRIPTION OF THE DRAWINGS

For a better understanding of the present invention, and to show more clearly how the same may be carried into effect, reference will be made to the accompanying drawings.

FIG. 1 is a schematic illustration of using a proteinase agent to create a harmless cancer vaccine capable of inducing immune responses against cancer cells.

FIG. 2 is a schematic illustration of using the cancer vaccine for cancer prevention in healthy or high-risk pre-cancer individuals and the use of the vaccine or the cancer vaccine specific immune components to kill cancer cells.

FIG. 3 is a tumor growth chart showing cancer vaccine vaccinated male mice induced immune responses against tumor cancer cells vs. unvaccinated male mice which did not induce immune responses against cancer cells' malignant tumor growth.

FIG. 4 is a tumor growth chart showing cancer vaccine vaccinated female mice induced immune responses against cancer cells' tumor growth vs. unvaccinated female mice which did not induce immune responses against cancer cells' malignant tumor growth.

FIG. 5 is a tumor growth chart showing cancer vaccine vaccinated mice induced immune responses against cancer cells' tumor growth vs. normal cell "vaccine" vaccinated mice and unvaccinated mice which did not induce immune responses against cancer cells' malignant tumor growth.

FIG. 6 shows that proteinase K-treated cancer vaccines form round-shaped "giant liposome" (cancer vaccine spheres) with unbroken lipid membrane, which is critical for keeping cancer specific antigens inside the cancer vaccines.

DETAILED DESCRIPTION OF THE INVENTION

Vaccine refers to a harmless variant or derivative of a pathogen that is presented to the body in order to induce an immune response against the pathogen. A cancer vaccine refers to harmless variants or derivatives of cancer cells that are presented to the body in order to induce immune responses against cancer cells for cancer prevention or immunotherapy of active cancers. The cancer vaccine is composed of variants or derivatives of cancer cells because cancer cells are heterogeneous and mutating cells that are not a clone of the same cells or a mixture of several cancer clones. Thus, a cancer vaccine induces immune responses (not a single immune response) against cancer cells. Furthermore, a singer cancer vaccine may induce limited immune responses depending on the mutation information contained in the vaccine.

The cancer mutation information is built into the cancer cells' heterogeneous and unstable genomes and expressed in their gene expression patterns including but not limited to one to tens of onco-gene expressions, loss of the tumor-suppressor gene expressions, production of microRNAs that promote tumor formation and expression of tumor-associated antigens and immune suppressing genes. Therefore, one cancer vaccine may induce immune responses to kill the majority of cancer cells from which the cancer vaccine is derived from, but the immune responses may not be able to kill all cancer cells if cancer cells mutate further beyond the information contained in the cancer vaccine.

Cancer vaccine is still a concept because there is no successful example yet. Gardasil and Cervarix are vaccines used to prevent cancer such as cervical cancer caused by the human papillomavirus (HPV). These vaccines are not cancer vaccines because they are not derivatives of any cancer cells and cannot be used to induce any immune responses against cancer cells including cervical cancer cells. When they are presented to the body, Gardasil and Cervarix induce an immune response against the HPV virus and to prevent the HPV viral infection and associated diseases including cervical cancer. Thus, to qualify as a cancer vaccine, first it has to be variants or derivatives of cancer cells or tumor tissues. Secondly, it has to be harmless to normal or healthy cells or the body and does not transform any normal cells to cancer cells. Thirdly, it must have the capability to induce immune responses against cancer cells.

So far, there is no successful example although many "cancer vaccines" have already advanced to late stage clinical trials. One possible reason for the failure of "cancer vaccines" is that the tested "cancer vaccines" might not induce immune responses because their self-recognition molecular patterns prevent them from being recognized by, or presented to, the immune system. Other possible reasons may be one or the combination of the following: 1) cancer cells were killed by γ-ray to make "cancer vaccines" harmless. However, the γ-ray fragmented DNA (into small pieces) may never match the genetic mutation information in target cancer cells. The "cancer vaccines" may thus confuse the immune system. 2) γ-rays may also cause protein cross-links that do not match antigens on the cell surface, in cell membrane or inside target cancer cells. 3) the self-recognition molecular patterns on the cell surface of "cancer vaccines" are different from normal cells of test animal models and induce strong immune responses in animal models but not in human beings. If "cancer vaccines" were effective, other factors including the over-expression of the self-recognition molecular patterns, cytokines and interleukins by malignant solid tumor organs may still prevent or suppress the immune responses.

A malignant tumor organ with a solid-structured main tissue and sporadic tissues might be more complicated than what we currently understand scientifically, physiologically and systemically. Indeed, many mechanisms at the body system level are different from mechanisms at the organ, tissue, cell and molecular levels due to compartmentation, blood flow direction and cycling, and interactions among different organs. The mutating and heterogenic nature of cancer cells may be the root of the problem. This information has to be entered and remembered by the immune system in order for the system to work against cancer cells for prevention and potential cure of cancer.

The term "dead cancer cells", as used herein, refers to cancer cells that irreversibly lose the ability to maintain an essential life function so that they can not grow or proliferate in vitro and in vivo, but not necessarily have the cell membrane compromised. The term "dead cancer cell spheres", as used herein, refers to dead cancer cells that irreversibly lose the ability to grow or proliferate in vitro and in vivo, but maintain the integrity of the cell membrane and have a shape of a sphere. In particular, the dead cancer cell spheres of the invention refer to dead cancer cells killed by proteinase digestion of vital membrane proteins and extracellular matrix proteins, which lose the original cell shape and are rounded up to form a sphere. The term "cancer vaccine spheres", as used herein, refers to dead cancer cell spheres that can effectively elicit immune responses to cancer cells in the body. For example, cancer vaccine spheres can be prepared by using proteinases to completely digest vital membrane proteins and extracellular matrix proteins of cancer cells, which results in dead cancer cell spheres with a "naked" cell membrane devoid of any surface recognition proteins. These cancer vaccine spheres with "naked" cell membrane are recognized by the immune system as non-self or foreign objects, leading to exposure and presentation of cancer-specific antigens inside the cancer vaccine spheres and elicitation of strong cancer-specific immunological responses.

Proteinases are used to make cancer vaccine spheres by incubating with cancer cells extracellularly, cleaving vital cell surface proteins and extracellular matrix proteins, and rendering the cancer cells dead or harmless while maintaining the integrity of the plasma membrane. Any proteinase or combination of proteinases that can effectively cleave cell surface proteins and extracellular proteins while maintaining the plasma membrane integrity can be used to make cancer vaccines. The concentration of proteinase(s) and incubation time and temperature can be varied to obtain optimal results as follows.

A, incubate cancer cells or tumor tissue with different concentrations of a proteinase in PBS or water at 37° C.

B, observe the morphologic changes of treated cancer cells under a microscope at different time points.

C, collect cancer cell spheres as the cancer vaccine when the cancer cells are completely detached from the culture dish, separated from each other, and rounded up to form spheres, which still maintain the integrity of the plasma membrane. Optionally, the integrity of the cell membrane can be tested by membrane permeable dyes.

D. confirm and verify that the cancer vaccine spheres lose the ability to grow or proliferate under normal culture conditions.

Proteinases that can be used to make cancer vaccines can be selected as described above. Many proteinases such as Tumorase™, proteinase K, pronase, trypsin can serve this purpose. Some are more efficient than others. For example, trypin is a milder proteinase than proteinase K, and it needs to incubate for a longer period of time to kill cancer cells and make cancer vaccine spheres. Strong proteinases like Tumorase™, proteinase K and pronase are preferable candidate proteinases.

Tumorase™ was used to make cancer vaccine spheres by incubating with cultured cancer cells until the cancer cells were completely detached from the culture dish, separated from each other and became individual round-shaped "giant liposome". The cell shape is close to perfect sphere shape and the cell size is significantly increased as well (see FIG. 6). 120 nude mice (60 males and 60 females) did not grow any tumor after they were injected with $4 \times 10^6$ above Tumorase™-treated cancer vaccine spheres with intact cell membranes[2]. It was not known if they could induce immune responses against cancer cells because nude mice did not have intact immune systems. Thus, wild-type mice are used to test if Tumorase™-treated cancer vaccine spheres can induce immune responses against genetically compatible wild-type mice cancer cells from which the cancer vaccine spheres were derived.

Because self-recognition molecular patterns including major histocompability complex (MHC) are cell surface proteins, a proteinase that digests self-recognition molecular patterns can be used to digest tissue-cultured cancer cells' surface proteins and extracellular matrix proteins and to make cancer vaccines conveniently. The proteinase may also be used to digest cancer cells or tumors from a cancer patient directly to make personalized cancer vaccine spheres that may trigger immune responses to specific to cancer cells of the same type.

FIG. 1 is a schematic illustration of using a proteinase agent to create a harmless cancer vaccine capable of inducing immune responses against cancer cells. Cancer cells may be from tissue cultures or tumors of a cancer patient directly. If they are from tissue cultures, cancer cells are grown in flasks with appropriate medium, serum, pH, temperature, $CO_2$ concentration and humidity for optimal growth. When cancer cells are crowded, the medium is decanted and washed them with a buffer or a small amount of a proteinase solution to eliminate proteinase inhibitors and to generate an optimal condition for the action of the proteinase agent. The proteinase agent cleaves peptide bonds on extracellular matrix proteins C-terminally, N-terminally or both depending on the species and the number of proteinases used. Cancer cells are separated individually and released from the container walls or adjacent cells as well. These cancer cells are briefly centrifuged to pellet and the supernatant is decanted. The pellet is re-suspended and washed two more times with phosphate buffer saline (PBS) and repeated centrifugation to eliminate amino acids, peptides and the proteinase agent completely. If cancer cell derivatives are dead as seen with the Tumorase™ treatment, they can be used as a cancer vaccine directly. If the cells are still alive as seen with the trypsin treatments, cancer cell derivatives can be further processed to make the cancer vaccine harmless by treating with the same proteinase or different proteinase until all the cancer cells are dead. If cancer cells are from tumors of a cancer patient directly, a biosurgery or a biochemotherpy[1, 2] may be used to obtain cancer cells. A large tumor or multiple tumors from a conventional surgery of a cancer patient may also be treated with a proteinase such as Tumorase™ to make a harmless cancer vaccine spheres. The cancer patient may be human or any animal under medical care.

FIG. 2 is a schematic illustration of the use of cancer vaccine and the cancer specific immune components to prevent cancer and to kill existing cancer cells. A cancer vaccine can be directly used to vaccinate healthy individuals or pre-cancer high risk individuals to induce the production of immune components ready for immune responses against cancer cells. The cancer vaccine specific immune components may be isolated from the vaccinated individuals via their blood draw or donation. Concentrated or purified cancer vaccine specific immune components including polyclonal antibodies, B-cells, macrophages, T-cells and other lymphocytes may be injected to a cancer patient's blood directly for immunotherapy against cancer cells. Vaccinated individuals may be human or animals including, but not limited to, mouse, dog, cat, hamster, horse, rabbit, rat, chicken, cow, tiger, panda, pig, sheep and monkey.

FIG. 3 is a tumor growth chart showing cancer vaccine vaccinated male mice induced immune responses against tumor cancer cells vs. unvaccinated male mice which did not induce immune responses against cancer cells' malignant tumor growth.

FIG. 4 is a tumor growth chart showing vaccinated female mice induced immune responses against tumor cancer cells vs. unvaccinated female mice which did not induce immune responses against cancer cells' malignant tumor growth.

Detailed experimental procedures for cancer cell culture, cancer vaccine small-scale production, cancer vaccine vaccination, cancer cell injection, and tumor measurement are as follows.

A mouse melanoma tumor cell line (CRL-6475, ATCC, Manassas, Va.) has been cultured in flasks containing 60 ml Eagle's Minimum Essential Medium (30-2003, ATCC, Manassas, Va.) with 5% fetal bovine serum USDA Premium (9871-5200, USA Scientific, Ocala, Fla.) under conditions previously described[2]. Crowded cancer cells were separated by 0.25% 1× Trypsin (Invitrogen, Carlsbad, Calif.) and subcultured. Tumorase™ (Biomedicure, San Diego, Calif.) in PBS was used to treat the subcultured cancer cells to make a cancer vaccine. Briefly, cancer cells were incubated with appropriate amounts of Tumorase™, preferably 0.1-10 mg/ml, at 37° C. and observed under a microscope. The cancer cells were collected as cancer vaccines when they were completely detached from the culture dish, separated from each other and became individual round-shaped "giant liposomes" (cancer vaccine spheres). The cancer vaccine spheres were then washed three times with PBS and centrifuged at 1000 rpm for 10 minutes using a clinical centrifuge. The cancer vaccines contained about $2 \times 10^7$ dead cancer cell spheres per 1 ml. They can be used immediately or stored at −20° C. for future use.

Wild-type mice (B16-F10, 23 days old) were purchased from Charles River (Hollister, Calif.) and delivered to the ovarium facility at Bio-Quant, Inc (San Diego, Calif.). Five male mice (31 days old) and five female mice (31 days old) were sub-Q injected with the $2 \times 10^6$ cancer vaccine spheres in 100 uL PBS three times when the mice were 31, 38 and 45 days old (vaccinated group). Other 5 male and 5 female mice (the same age) did not receive any cancer vaccine injection and served as control groups.

The same melanoma tumor cell line (as was used to make cancer vaccine) was cultured and harvested with 0.25% trypsin solution and used to grow tumors in both vaccinated and unvaccinated mice (20) randomly. About $1 \times 10^6$ live cancer cells were injected to induce tumor formation via sub-Q on each of two sites of the flank of a randomly selected 54-day-old mouse.

Tumors were two dimensionally measured using an electronic caliper on days 6, 8 and 11 after cancer cell injections. Tumor volume was calculated by $\frac{1}{2} ab^2$ in $mm^3$ volume where "a" represents the tumor length in mm and "b" is the tumor width in mm measured.

In FIG. 3, the unvaccinated male control group had tumors grew faster 8 days after the cancer cell injection than those of the cancer vaccine vaccinated male group. The average tumor volume for the unvaccinated male control group was about 702 $mm^3$ while the average tumor volume for the vaccinated male group was about 250 $mm^3$ 11 days after the cancer cell injection.

The unvaccinated female control group had tumors grew faster 8 days after the cancer cell injection than those of the cancer vaccine vaccinated female group. The average tumor volume for the unvaccinated female control group was about 715 $mm^3$ while the average tumor volume for the cancer vaccine vaccinated female group was about 264 $mm^3$ 11 days past the cancer cell injection.

Thus, the average tumor volume for the unvaccinated control groups (5 males and five females) were about 708 $mm^3$ while the average tumor volume for the cancer vaccine vaccinated groups (5 male and 5 females) were about 257 $mm^3$ 11 days past the cancer cell injection (FIG. 4).

The cancer vaccine vaccination have induced vaccinated animals' immune responses against cancer cells (1 million per site, 2 million per animal) injected by sub-Q. Because there was no tumor grown on any vaccinated mice before cancer cell injection and there were no significant weight changes for any vaccinated animals when compared with unvaccinated animals (data not shown), the cancer vaccine did not show any adverse effects.

FIG. 5 further showed that cancer vaccine vaccinated male and female mice have induced immune responses against cancer cells' malignant tumor growth while normal cell "vaccine" vaccinated mice and unvaccinated mice did not induce immune responses against cancer cells' malignant tumor growth. The normal cell "vaccine" was made by the same procedure used to make cancer vaccine except using tissue-cultured cells from a normal mouse epidermis cell line (CRL-2007, ATCC, Manassas, Va.). Details of experiment procedures are similar to those of the previous experiment.

Nine mice (4 males, 5 females, 65 days old) were sub-Q injected with the same cancer vaccine (about 1.75 million dead cancer cells per mice) in 100 μL PBS 5 times when the mice were 65, 72, 79, 86 and 91 days old (cancer cell vaccinated group).

Nine mice (4 males, 5 females, 65 days old) were sub-Q injected with the normal cell derived "vaccine" (about 2.6 million dead cells per mice) in 100 uL PBS 5 times when the mice were 65, 72, 79, 86 and 91 days old (normal cell vaccinated group).

Nine mice (4 males, 5 females, 65 days old) were sub-Q injected with 100 uL PBS 5 times when the mice were 65, 72, 79, 86 and 91 days old (unvaccinated control group).

The same melanoma cancer cell line described in the previous experiment was prepared and used to sub-Q inject each of the 27 mice randomly selected when they were 105 days old. Every mouse had about $1 \times 10^6$ live cancer cells injected in 100 uL PBS suspensions to induce tumor formation.

Tumors were two dimensionally measured with an electronic caliper on days 7, 9 and 11 after cancer cell injections. Tumor volume was calculated the same way as described above.

In FIG. 5, the normal cell derived "vaccine" vaccinated mice showed similar tumor growth curve to that of the control without any vaccination. On day 11 after the cancer cell injection, the cancer vaccine vaccinated group showed significantly lower average tumor volume (about 155 mm$^3$) than that of control (about 653 mm$^3$) and that of normal cell "vaccine" control (about 663 mm$^3$). However, the average tumor volume between the unvaccinated and the normal cell "vaccine" vaccinated animal groups were not significantly different at any point recorded.

When comparing results from the first experiment (FIG. 4) and the second experiment (FIG. 5), the average tumor volume for control groups at different experiments was similar. However, the cancer vaccine vaccinated group with 5 vaccinations in 5 consecutive-weeks (FIG. 5) showed better immune responses than the group vaccinated 3 times in 3 consecutive-weeks (FIG. 4). This is reasonable because the longer the cancer vaccine presented to the mice, the more mutation information in the cancer vaccine may be entered into mice's immune system and stronger immune responses have been shown. Vaccinated animals not only have smaller tumors but also have movable tumors which be easily eliminated by Tumorase™ biochemotherapy or conventional operations. Furthermore, multiple cancer vaccines' vaccinations may enable the vaccinated acquire total immunity against all cancer cells in the tumor.

The cancer vaccines derived directly from patients' tumor tissue have been used to treat patients with different types of cancers. Preliminary trials of treating cancer patients with cancer vaccines has achieved exceptionally successful and promising results. Most of the cancer patients volunteered to participate in the clinical treatment with cancer vaccines are patients at the advanced/metastatic stage of their cancer who cannot find effective treatment means with traditional methods such as radiotherapy, chemotherapy and surgery. Customized cancer vaccines were prepared from tumor tissues of each patient by treating patient tumor tissue with Tumorase™ as described above and injected into the same patient. All the cancer patients who have healthy, non-damaged immune systems have shown significant improvement with only one or two treatments of cancer vaccines. It is even more impressive that 40% of cancer patients have survived the cancer up to the present (at least one year after the treatment), who are capable of independent living with no detectable tumors, no detectable micro tumors, no detectable cancer cells and no symptoms of cancer, and have cancer marker levels within normal range. A few typical patient treatment cases are provided below and table 1 summarizes the results of cancer vaccine treatment from 35 cancer patients.

1. Ms. Huo, age 49, a breast lump about 1 cm$^3$ was found in her right side breast during a physical examination on September, 2011. Two months later, the lump size increased to 4 cm based on type-B ultrasonic check and she was diagnosed with breast cancer. On Nov. 7, 2011, modified radical mastectomy was performed in the hospital, pathology report after the surgery indicated it as breast invasive ductal carcinoma grade II-III, axillary lymph node 1/26, ER (−), PR (−), HER2 (+++). On Nov. 21, 2011, the patient was examined in the Affiliated Hospital of Fudan University, multiple lesions were found in liver, so diagnosed with liver metastasis; three metastatic lesions were 4 cm, 2 cm and 2 cm, respectively. After two weeks chemotherapy, the liver metastatic tumors did not show any significant shrinkage. The patient was told by several cancer experts at Shanghai that she probably only had 3 more months left, because there're actually many invisible cancer cells already spread all over her body. On December 2011, at her request, BioMedicure prepared cancer vaccine which can be only used to treat this patient. Two months after cancer vaccine treatment, CT exam found that two metastatic tumors had disappeared; only one tumor shadow was visible. So again tissue sample was taken from this shadow and pathology test showed that this shadow is caused by the infiltration of inflammatory cells. The patient has been taking check-up regularly, and up to the present (October, 2014) no abnormalities were found with tumor marker test and imaging examination.

2. Mr. Ma, age 55, was diagnosed with primary heptocellular carcinoma in the Eastern Hepatobiliary Hospital on Jan. 10, 2011. The tumor size was 19×19 cm at the right liver. After surgery, hepatic artery interventional therapy was performed in the Eastern Hepatobiliary Hospital on Feb. 25, 2011. The follow-up exams on Sep. 28, 2011 showed AFP level was 47 ug/L, and enhanced MRI found widespread metastasis, including local recurrence and intestinal ventral diaphragm and abdominal cavity. The patient took gamma knife treatment on Oct. 1, 2011 at The 455 Hospital of PLA. To remove the intestinal obstruction, the patient again took an operation on Oct. 26, 2011. At the same operation, several larger tumors were removed, left some relatively smaller ones. Some removed tumor tissues were sent to BioMedicure Engineering Center. BioMedicure prepared the cancer vaccine for Mr. Ma at his request. After one course of treatment, his health recovered; the immune system including the counts of lymphocyte gradually returned to normal. It's been two years that no abnormalities are found; alpha fetoprotein (AFP) level is within normal range, abdominal CT examination showed no tumor recurrence and metastasis.

3. Ms. Jin, age 63, comes from Nantong, Jiangsu. She went to The 85 Hospital of PLA because of abdominal discomfort and was diagnosed with pancreatic cancer in March 2012. In March 2012, the surgery removed pancreatic body and tail, gallbladder and spleen. Some removed tumor tissues were sent to BioMedicure Engineering Center. At her request, BioMedicure prepared the cancer vaccine for her. After one course of treatment, the patient regained her health. So far, the patient is doing well, sleeping and eating normally. No abnormalities were found with tumor marker test and imaging examination.

4. Mr. Yang, age 52, due to fatigue and worsened back pain, he was diagnosed with nodular hepatocellular carcinoma at the right lobe of liver in 2012 March. The size of tumor was about 4.4×3.6 cm. The patient was also diagnosed with hepatitis B cirrhosis. After the surgery in Apr. 16, 2012, the patient's tumor tissues were promptly sent to BioMedicure Engineering Center. At his request, BioMedicure prepared the cancer vaccine for him. Without any other treatment, at the end of one course of the cancer vaccine treatment, the patient's liver function returned to normal and fully covered from hepatitis B (Test results showed that hepatitis B DNA is less than 1.00×10^3 copies/ml, within the normal reference range). No abnormalities were found with tumor marker test and imaging examination. So far, the patient is doing well, sleeping and eating normally, and has returned to normal life and work.

5. Mr. Li, age 45, because of the right thyroid lesions, solid mass on the left side of the neck, and enlargement of thyroid, he was diagnosed with thyroid tumor in April 2011. The patient had surgery of thyroidectomy and the pathological test showed it was thyroid papillary carcinoma. 10 months later because of the cancer metastasis to left neck lymph node, the patient was hospitalized again and had surgery for lymph node dissection. Since 2011, the patient has suffered from hoarseness. On Feb. 18, 2013, the patient had breathing difficulties with aggravated hoarseness. Two days later, because of the breathing difficulties, tracheotomy intubation was performed. And the examination showed lymph node metastasis at the neck, bilateral vocal cord paralysis. On Feb. 28, 2013, needle biopsy was done at the left neck lymph node. At the patient's request, a part of the tumor tissues were sent to BioMedicure Engineering Center for the preparation of the cancer vaccine. On Apr. 12, 2013, a partial resection of the lymph node at right neck was done, part of the tumor tissues were again sent to BioMedicure Engineering Center for making cancer vaccine. On May 20, 2013, the follow-up exam showed only right vocal cord paralysis. CT test in neck showed significant shrinkage of lymph nodes. No more breathing discomforts after tracheal intubation were pulled out. After three months of cancer vaccine treatment, the symptoms such as breathing difficulties and vocal cord paralysis had been greatly improved.

6. Ms. Wu, age 50. At Oct. 23, 2013, she was hospitalized and had surgeries of hysterectomy plus oophorectomy, and bilateral pelvic lymph node dissection and abdominal aortic anterior lymph node biopsy. Her discharge diagnoses are: 1. Cervical squamous cell carcinoma stage Ib2; 2. Uterine leiomyoma; 3. HPV infection; 4. Hypertension. In November 2013, Ms. Wu requested BioMedicure to prepare cancer vaccine for her. After one month of radio-therapy, she took the cancer vaccine treatment for one and half month. Her level of CA125 dropped to normal range. However, since the CA19-9 level was still above normal after radio-therapy, she asked BioMedicure to prepare the cancer vaccine for her again in February 2014. After the second cancer vaccine treatments, her CA19-9 level has dropped to normal level. So far all her physical indexes and tumor markers were normal.

7. Ken R., American, male, age 61, diagnosed with advanced gastric cancer with widespread metastatic signet ring in United States on Mar. 6, 2014. The patient suffered a sharp decline in body weight: lost about 10 pounds in one month and the life expectancy were only three months. Due to strong side effects, chemotherapy had to be terminated after only one treatment. On May 19 in a Chinese hospital, the patient was diagnosed again as low differentiation cancer cell infiltration gastric carcinoma (T4N×M1). Peritoneal biopsy was done on May 20 and tumor metastasis was found in the whole abdomen. Metastasis cancer nodules from right upper peritoneum, liver ligament and omentum were taken for the preparation of cancer vaccine. After the cancer vaccine treatment, the patient body weight stopped dropping and recovered to the level of previous month. On July 7, laparoscopic biopsy was done in a Chinese hospital, and the metastatic tumor samples were taken to make the cancer vaccine for his second treatment. On September 2, when endoscopy was performed in a United States hospital, no stomach tumors were observed. But still there are local thickening of the stomach wall, and peritoneal tumor metastasis. The patient requested for the third cancer vaccine treatment. The patient has lived a much better life than before the cancer vaccine treatment.

TABLE 1

Summary of Cancer Patient Cases treated with Cancer Vaccines

| Cancer Type | # Patients | # Case with Improvement* | % Improvement Case | Prolonged Life Span* | # Cured Case** | % Cured Case |
|---|---|---|---|---|---|---|
| Pacreatic Cancer | 5 | 3 | 60 | >6 months | 2 | 60 |
| Liver Cancer | 7 | 4 | 57.1 | >12 months | 3 | 42.9 |
| Colorectal Cancer | 6 | 3 | 50 | >12 months | 3 | 50 |
| Stomach Cancer | 5 | 3 | 60 | >12 months | 2 | 40 |
| Esophageal Cancer | 3 | 2 | 66 | >12 months | 1 | 33 |
| Lung Cancer | 3 | 3 | 100 | >12 months | 0 | 0 |
| Cervical Cancer | 3 | 1 | 33 | >12 months | 2 | 67 |
| Breast Cancer | 3 | 2 | 67 | >12 months | 1 | 33 |
| Total | 35 | 21 | 60 |  | 14 | 40 |

*Cases with improvement refer to the patient cases where the patients have prolonged life span, improved quality of life and no pain at the end of their lives. The prolonged life span in column 5 of the table 1 refers to the patient cases with improvement, not the cured cases.
**Cured cases refer to the cases where the patients have survived the cancer up to the present who are capable of independent living with no detectable tumors, no detectable micro tumors, no detectable cancer cells and no symptoms of cancer, and have cancer marker levels within normal ranges.

Even with only the preliminary clinical data, the advantages of the cancer vaccine treatment of the invention are very clear. The cancer vaccine treatment is effectively applicable to different cancer types. The only requirement is that the patient has a relatively healthy immune system. It is a customized treatment that specifically targets cancer cells in the patient with little side effect towards normal cells. The treatment involves no chemicals or procedures harmful to the health of cancer patients, which results in faster and smoother recovery. The cancer vaccine treatment has been the first cancer therapy that can effectively treat many different cancer types at advanced and metastatic stages. This method not only prolongs the life span and significantly improves the life quality of late stage cancer patients, but also brings 40% of these patients back to cancer-free lives with no detectable tumors, no detectable micro tumors, no detectable cancer cells and no symptoms of cancer. The cancer vaccine therapy of the invention is a revolutionary cancer treatment that is universal, effective, and with minimal side effects. A related Chinese patent application (ZL 200880023432.7), entitled "Proteinases destroy cancer tumor's solid structure and kill cancer cells locally", was issued on Jan. 15, 2014. Expedite prosecution of this patent application will facilitate the widespread application of this revolutionary cancer therapy and bring new light and hope to all cancer patients, especially patients with advanced cancers.

Although the detailed mechanism of immune responses induced by the cancer vaccine is unknown, the following factors could contribute the exceptional effectiveness of the cancer vaccine. First of all, the cancer vaccine spheres with "naked" cell membrane is recognized as non-self or foreign to the immune system because their cell surfaces do not have the self-recognition moleculars (cleaved off by proteinases during the preparation process). This enables lymphocytes including dendritic cells and macrophages to recognize them, sample them and present their antigen profile to the immune system. Secondly, the mutation information in the cancer vaccine might be presented to T-cells through antigen-presentation processes by dendritic cells and macrophages. Thirdly, the mutation information within the antigen profile was compared to those in normal cells, retained and memorized by B-cells. Fourthly, polyclonal antibodies against cancer vaccine specific antigens might be produced. In the presence of living cancer cells, polyclonal antibodies may bind to cancer cells to induce antibody-dependent cellular cytotoxicity (ADCC). Furthermore, the presence of cancer cells may also trigger the proliferation of lymphocytes including B-cells, T-cells and natural killer cells and more polyclonal antibodies production to immune against cancer cells.

In addition to Tumorase™, other proteinases including carboxypeptidase B, elastase, plasmin, endoproteinase Glu-C, endoproteinase Asp-N, endoproteinase Lys-C, endoproteinase Arg-C, chymotrypsin, or carboxypeptidase Y, caspases, proteinase K, subtilisin BL, M-protease, thermitase, subtilisin Carlsberg, subtilisin Novo BPN', subtilisin BPN', selenosubtilisin, tonin, blood coagulation factor XA, rat mast cell protease II, kallikrein A, pronase, trypsin, anhydrotrypsin, beta-trypsin, alpha-chymotrypsin, gamma-chymotrypsin, elastase, tosyl-elastase, human neutrophil elastase, human leukocyte elastase, alpha-thrombin, gamma-thrombin, epsilon-thrombin, glutamic acid specific protease, achromobacter protease I, alpha-lytic protease, proteinase A, proteinase B, actinidin, cathepsin B, papaya protease omega, papain, interleukin 1-beta converting enzyme, myeloblastosis associated viral protease, rous sarcoma virus protease, simian immunodeficiency virus protease, HIV-1 protease, HIV-2 protease, cathepsin D, chymosin B, endothiapepsin, penicillopepsin, pepsin, pepsin 3A, renin, rhizopuspepsin, neutral protease, thermolysin, astacin, astacin (zinc replaced by Cu2+), astacin (zinc replaced by cobalt2+), astacin (zinc replaced by mercury2+), astacin (zinc removed), astacin (zinc replaced by nickel2+), serralysin (bound to zinc), collagenase, fibroblast collagenase and neutrophil collagenase might also be used to make cancer vaccines out of cancer cells if they can effectively change the self-recognition molecular patterns on cancer cell surfaces and kill cancer cells without breaking the integrity of the cell membrane. A single proteinase or a combination of proteinases suitable for making cancer vaccines can be selected using the methods described above.

Because a cancer vaccine can induce immune responses against cancer cells, limiting the growth of tumors but not killing all cancer cells, it is appropriate to use a proteinase biochemotherapy to disrupt or destroy the solid-structure of the tumor and systemically kill all cancer cells. Although the site-specific proteinases themselves may not be able to kill cancer cells, additional immune responses will kill living cancer cells with changes on their self-recognition molecular patterns. Thus, a combination of cancer vaccine or vaccines with less toxic proteinase's biochemotherapy on tumors has great potential to eliminate cancer cells from human or animal.

Because cancer vaccine can induce immune responses against cancer cells, the vaccine can be used to prevent cancer in healthy individuals or pre-cancer high-risk individuals. These individuals may be human or animals if cancer vaccines were made from tissue-cultures of human or animal cancer cell lines selected from the following (next 4 pages): human cancer cell lines including cervix adenocarcinoma (HeLa, ATCC), colon adenocarcinoma (TAC-1, ATCC), duodenum adenocarcinoma (HuTu 80, ATCC), endometrium uterus adenocarcinoma (KLE, ATCC), kidney adenocarcinoma (A704, ATCC), lung adenocarcinoma (NCI-H1373, ATCC), mammary gland adenocarcinoma (Hs 274.T, ATCC), ovary adenocarcinoma (Caov-3, ATCC), pancreas adenocarcinoma (BxPC-3, ATCC), rectum adenocarcinoma (SW837, ATCC), lung bronchogenic adenocarcinoma (Hs229.T, ATCC), cecum colorectal adenocarcinoma (NCI-H716, ATCC), colon colorectal adenocarcinoma (HCT-15, ATCC), rectum colorectal adenocarcinoma (SW1463, ATCC), pancreas ductal adenocarcinoma (PL45, ATCC), transfected prostate adenocarcinoma (CA-HPV-10, ATCC), stomach gastric adenocarcinoma (AGS, ATCC), non-small cell lung cancer adenocarcinoma (NCI-H23, ATCC), kidney renal adenocarcinoma (ACHN, ATCC), mammary gland scirrhous adenocarcinoma (Hs 742.T, ATCC), skin hereditary adenomatosis (182-PF SK, ATCC), kidney angiomyolipoma (SV7tert, ATCC), brain astrocytoma (CCF-STTG1, ATCC), nipple breast cancer (HT 762.T, ATCC), lung cancer (Hs 573.T, ATCC), non-small cell lung cancer (NCI-H2135, ATCC), mammary gland cancer (Hs 319.T, ATCC), colon colorectal cancer (Hs 675.T, ATCC), lung carcinoid (NCI-H835, ATCC), cortex adrenal gland carcinoma (NCI-H295R, ATCC), urinary bladder carcinoma (Hs 195.T, ATCC), cervix carcinoma (C-4 I, ATCC), kidney carcinoma (A-498, ATCC), lung carcinoma (A549, ATCC), mammary gland carcinoma (Hs 540.T, ATCC), ovary carcinoma (Hs 38.T, ATCC), pancreas carcinoma (MIA PaCa-2, ATCC), prostate carcinoma (22Rv1, ATCC), stomach carcinoma (Hs 740.T, ATCC), endometrium uterus carcinoma (RL95-2, ATCC), lung adenosquamous carcinoma (NCI-H596, ATCC), cortex adrenocortical adrenal gland carcinoma (NCI-H295, ATCC), lung alveolar cell carcinoma (SW 1573, ATCC), skin basal cell carcinoma (TE 354.T, ATCC), lung classic small cell lung cancer carcinoma (NCI-H1688, ATCC), kidney clear cell carcinoma (Caki-2, ATCC), ovary clear cell carcinoma (ES-2, ATCC), cecum colorectal carcinoma (SNU-C2B, ATCC), colon colorectal carcinoma (HCT 116, ATCC), rectum colorectal carcinoma (Hs 722.T, ATCC), mammary gland ductal carcinoma (UACC-812, ATCC), testis embryonal carcinoma (Cates-1B, ATCC), epidermoid carcinoma (A-431, ATCC), lung epidermoid carcinoma (HLF-a, ATCC), duct pancreas epithelioid carcinoma (PANC-1, ATCC), stomach gastric carcinoma (SNU-1, ATCC), liver hepatocellular carcinoma (SNU-398, ATCC), medulla thyroid carcinoma (TT, ATCC), liver pleomorphic hepatocellular carcinoma (SNU-423, ATCC), mammary gland primary ductal carcinoma (HCC38, ATCC), mammary gland primary metaplastic carcinoma (HCC1569, ATCC), small cell lung cancer carcinoma (DMS 53, ATCC), cervix squamous cell carcinoma (SW756, ATCC), lung squamous cell carcinoma (SW 900, ATCC), pharynx squamous cell carcinoma (FaDu, ATCC), thyroid squamous cell carcinoma (SW579, ATCC), tongue squamous cell carcinoma (SCC-15, ATCC), vulva squamous cell carcinoma (SW 954, ATCC), urinary bladder transitional cell carcinoma (UM-UC-3, ATCC), ureter transitional cell carcinoma (Hs 789.T, ATCC), bone chondrosarcoma (Hs 819.T, ATCC), placenta chondrosarcoma (JAR, ATCC), skin dermatofibrosarcoma (Hs 357.T, ATCC), skin dermatofibrosarcoma protuberans (Hs 295.T, ATCC), erythroblast bone marrow erythroleukemia (TF-1, ATCC), connective tissue fibrosarcoma (HT-1080, ATCC), brain glioblastoma (A172, ATCC), brain astrocytoma glioblastoma (U-118 MG, ATCC), brain p53 expression glioblastoma (LNZTA3WT4, ATCC), brain glioma (Hs 683, ATCC), glomus kidney glomangioma (glomotel, ATCC), bone eosinophilic granuloma (Hs 454.T, ATCC), lymph node noncaseating granuloma (Hs 697.Ln, ATCC), bone periostitis granuloma (Hs 709.T, ATCC), liver hepatoma (PLC/PRF/5, ATCC), connective tissue histiocytoma (Hs 856.T, ATCC), kidney hypernephroma (SW 156, ATCC), skin keratoacanthoma (Hs 892.T, ATCC), skin malignant acanthocytosis keratoacanthoma (Hs 898.T, ATCC), muscle leiomyosarcoma (TE 149.T, ATCC), uterus leiomyosarcoma (SK-UT-1, ATCC), vulva leiomyosarcoma (SK-LMS-1, ATCC), B lymphoblast acute lymphoblastic leukemia (SUP-B15, ATCC), myeloblast bone marrow acute lymphoblastic leukemia (KG-1, ATCC), T lymphoblast acute lymphoblastic leukemia (MOLT-4, ATCC), monocyte acute monocytic leukemia (THP-1, ATCC), peripheral blood acute myeloid leukemia (AML14.3D10, ATCC), promyeloblast acute promyelocytic leukemia (HL-60, ATCC), T lymphocyte acute T cell leukemia (J.CaM1.6, ATCC), peripheral blood chronic myeloblastic leukemia (Kasumi-4, ATCC), myelomonoblasktic leukemia (GDM-1, ATCC), lymphoblast myelmonocytic leukemia (CESS, ATCC), connective tissue liposarcoma (SW 872, ATCC), lymph node lymphogranulomatosis (Hs 268.T, ATCC), B lymphoblast lymphoma (1A2, ATCC), lymph node lymphoma (Hs 313.T, ATCC), cutaneous T lymphocyte lymphoma (HuT 78, ATCC), B lymphocyte Burkitt's lymphoma (EB-3, ATCC), B cell kidney Burkitt's lymphoma (HKB-11, ATCC), lymph node lymphocytic lymphoma (Hs 505.T, ATCC), peritoneal effusion B cell lymphoma (JSC-1, ATCC), upper maxilla Burkitt's lymphoma (EB1, ATCC), T lymphocyte cutaneous lymphoma (H9, ATCC), B lymphoblast EBV and KSHV positive lymphoma (BC-1, ATCC), macrophage histiocytic lymphoma (U-937, ATCC), lymph node lymphosarcoma (TE175.T, ATCC), cerebellum brain medulloblastoma (D341 Med, ATCC), skin melanoma (Hs 600.T, ATCC), skin amelanotic melanoma (C32TG, ATCC), connective tissue malignant melanoma (Hs 934.T, ATCC), skin malignant melanoma (A375.S2, ATCC), brain neuroblastoma (CHP-212, ATCC), neuroblast brain neuroblastoma (IMR-32, ATCC), brain neuroglioma (H4, ATCC), bone osteosarcoma (143.98.2, ATCC), connective tissue osteosarcoma (Hs 864.T, ATCC), pharynx papilloma (Hs 840.T, ATCC), B lymphocyte myeloma plasmacytoma (RPMI 8226, ATCC), bone marrow myeloma plasmacytoma (NCI-H929, ATCC), retina retinoblastoma (Y79, ATCC), connective tissue rhabdomyosarcoma (TE 441.T, ATCC), muscle rhabdomyosarcoma (A-673, ATCC), kidney renal rhabdomyosarcoma (Hs 926.T, ATCC), bone sarcoma (SK-ES-1, ATCC), bone giant cell sarcoma (Hs 706.T, ATCC), connective tissue giant cell sarcoma (Hs 127.T, ATCC), vertebral column giant cell sarcoma (Hs 814.T, ATCC), skin pagetoid sarcoma (Hs 925.T, ATCC), lymph node reticulum cell sarcoma (Hs 324.T, ATCC), connective tissue synovial sarcoma (Hs 701.T, ATCC), synovium sarcoma (SW 982, ATCC), uterus sarcoma (MES-SA/MX2, ATCC), bone Ewing's sarcoma (Hs 822.T, ATCC), ovary teratoma (TE 84.T, ATCC), bone sacrococcygeal teratoma (TE 76.T, ATCC), nullipotent stem cell teratocarcinoma (NCCIT, ATCC), cerebellum brain malignant primaitive neuroectodermal tumor (PFSK-1, ATCC), oral nonneoplastic tumor (Hs 53.T, ATCC), skin xanthogranuloma (Hs 156.T, ATCC); dog cancer cell lines including connective tissue cancer (CF17.T, ATCC), mammary gland cancer (CF33.MT, ATCC), bone osteosarcoma (D17, ATCC), connective tissue osteosarcoma (CF11.T, ATCC), macrophage histiocytosis (DH82ECOK, ATCC); cat cancer cell lines including bone marrow erythroleukemia (F25, ATCC), connective tissue fibrosarcoma (FC77.T, ATCC), spleen fibrosarcoma (FC81.Sp, ATCC), thymus fibrosarcoma (FC81.Thy, ATCC), lymph node lymphoma (F1B, ATCC) lymphoblast lymphoma (FL74-UCD-1, ATCC), spleen lymphoma (FC16.Sp, ATCC), connective tissue sarcoma (FC100.T, ATCC), spleen sarcoma (FC100.Sp, ATCC), bone marrow reticulum cell sarcoma (FC11.BM, ATCC), thymus osteosarcoma (FC95.Thy, ATCC); mouse cancer cell lines including mammary gland adenocarcinoma (JC, ATCC), pancreas adenocarcinoma (LTPA, ATCC), salivary gland adenocarcinoma (WR21, ATCC), kidney renal adenocarcinoma (RAG, ATCC), lung adenoma (LA-4, ATCC), connective tissue cancer (MM37T, ATCC), mammary gland cancer (MM2SCT, ATCC), colon carcinoma (CT26.WT, ATCC), Lewis lung carcinoma (LL/2, ATCC), lung squamous cell carcinoma (KLN 205, ATCC), bladder fibrosarcoma (MM45T.BI, ATCC), connective tissue fibrosarcoma (MM47T, ATCC), spleen fibrosarcoma (MM45T.Sp, ATCC), liver hepatoma (Hepa 1-6, ATCC), B lymphocyte leukemia (CW13.20-3B3, ATCC), spleen erythroblast leukemia (BB88, ATCC), B lymphocyte lymphoma (WEHI-231, ATCC), monocyte/macrophage lymphoma (P388D, ATCC), spleen lymphoma (RAW 309F.1.1, ATCC), T lymphocyte lymphoma (S1A.TB.4.8.2, ATCC), thymus T lymphocyte lymphoma (R1.1, ATCC), thymus lymphoma (EL4.IL-2, ATCC), mast cell mastocytoma (P815, ATCC), skin melanoma (B16-F10, ATCC), neuroblast brain neuroblastoma (NB41A3, ATCC), B lymphocyte myeloma plasmacytoma (P1.17, ATCC), connective tissue sarcoma (EHS, ATCC), B lymphocyte reticulum cell sarcoma (X16C8.5, ATCC), monocyte/macrophage reticulum cell sarcoma, (J774A.1, ATCC), testis teratocarcinoma (NULLI-SCC1, ATCC), keratinocyte teratoma (XB-2, ATCC); rat cancer cell lines including mammary gland adenocarcinoma (NMU, ATCC), small intestine adenocarcinoma (IA-XsSBR, ATCC), mammary gland cancer (Rn1T, ATCC), prostate cancer (R-3327-AT-1, ATCC), mammary gland carcinoma (DSL-6A/C1, ATCC), pancreas carcinoma (DSL-6A/C1, ATCC), prostate malignant carcinoma (AT3B-1, ATCC), nasal squamous cell carcinoma (FAT 7, ATCC), brain glioma (C6, ATCC), liver hepatoma (H4TG, ATCC), peripheral blood basophil leukemia (RBL-1, ATCC), central nervous system neuroblastoma (B35, ATCC), bone osteosarcoma (UMR-106, ATCC), adrenal gland pheochromocytoma (PC-12, ATCC); Syrian golden hamster skin malignant melanoma (RPMI 1846, ATCC); guinea pig colon colorectal adenocarcinoma (GPC-16, ATCC); chicken hepatocellular liver carcinoma (LMH, ATCC) and bursa lymphoma (DT40, ATCC); bovine cancer cell line including lymph node leukemia (2FLB.Ln, ATCC), B lymphocyte lymphosarcoma (BL3.1, ATCC), bone marrow lymphosarcoma (LB9.Bm, ATCC), spleen lymphosarcoma (LB10.Sp, ATCC), thymus lymphosarcoma (LB9.Thy, ATCC) and any other naturally occurring cancers from any species.

Due to genomic differences, cancer vaccines made from cancer cells of one species are useful only for the same species to fight against cancer cells. For example, human cancer vaccines made from human cancer cell lines or tumor lines must be used for human cancer prevention or treatment of cancer. Human cancer vaccines should not be used for any animal vaccinations, and vice versa. For an immune competent animal, human cancer vaccine or human cancer cells are both foreign and can induce immune responses. However, these immune responses are against human cancer cells, not against any animal cancer cells. Nevertheless, humanized antibodies against human cancer vaccines made from various systems including animals may be useful for human cancer patients' immunotherapy.

Another example is that cat cancer vaccines made from cat cancer cell lines will not prevent dogs' cancer, vice versa. Although a cat's cancer vaccine may induce immune responses in dogs, any cat's cancer never naturally occur in dogs. Thus, dogs vaccinated with a cat cancer vaccine may not prevent any dog cancer. Furthermore, human's breast cancer vaccine may not be used to prevent human's prostate cancer if the mutation profile in breast cancer vaccine antigens does not cover any prostate cancer cell associated antigens.

Because a cancer vaccine is harmless, multiple cancer vaccines' vaccinations may induce multiple immune responses against multiple cancers. Multiple sets of immune components isolated from individuals with multiple cancer vaccines' vaccination may be isolated for more effective immunotherapy on cancer. Immune components include, but are not limited to, polyclonal antibodies and activated lymphocytes such as B-cells, T-cells, macrophages, monocytes and natural killer cells. The cancer vaccine specific immune components may be obtained from the blood of vaccinated individuals. These immune components may be used to kill cancer cells for cancer patients who are compatible with blood donor's blood types but have a suppressed immune system that does not sufficiently respond to the cancer vaccine.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed:

1. A method of making a cancer vaccine for treating a cancer patient, and treating a cancer patient with the cancer vaccine, comprising:
   a) incubating proteinase K extracellularly with cancer cells in a culture dish;
   b) killing the cancer cells by using proteinase K to digest vital extracellular proteins, surface proteins and extracellular portion of membrane proteins of the cancer cells while maintaining the integrity of the plasma membrane of the cancer cells;
   c) collecting cancer cell spheres as said cancer vaccine when the cancer cells are completely detached from the culture dish, separated from each other, and rounded up to form cancer cell spheres, wherein said cancer cell spheres maintain the integrity of the plasma membrane of the cancer cells; and
   d) administering an effective amount of said cancer vaccine to a cancer patient to treat cancer.

2. The method of claim 1, wherein the cancer cells used to make the cancer vaccine are obtained from a cancer patient's tumor tissue or his/her cancer cells, wherein the cancer vaccine is used to treat the same cancer patient.

3. The method of claim 1, wherein proteinase K directly incubates with cancer cells isolated from patient's tumor tissue without pre-culture of the cancer cells.

4. The method of claim 1, wherein the cancer cells are isolated from patient's tumor tissue and cultured in vitro before subjected to proteinase K digestion.

5. The method of claim 1, wherein the cancer patient is a human being or other animals.

* * * * *